US00PP10036P

United States Patent [19]

Rother

[11] Patent Number: Plant 10,036

[45] Date of Patent: Sep. 23, 1997

[54] PETUNIA PLANT NAMED SUNSNOW

[76] Inventor: Reinhard W. Rother, 56 Emerald Monbulk Road, Emerald, Victoria 3782, Australia

[21] Appl. No.: 680,166

[22] Filed: Jul. 15, 1996

[51] Int. Cl.[6] ..... A01H 5/00

[52] U.S. Cl. ..... Plt./68.1

[58] Field of Search ..... Plt./68.1

*Primary Examiner*—James R. Feyrer

*Attorney, Agent, or Firm*—C. A. Whealy

[57] ABSTRACT

A distinct cultivar of Petunia plant named 'Sunsnow', characterized by its white flowers that are slanted upwards; compact growth habit; decumbent and spreading plant habit; freely branching habit; early flowering; very floriferous with numerous flowers per plant; and tolerance to rain, drought and temperature extremes.

2 Drawing Sheets

The present invention relates to a new and distinct cultivar of Petunia plant, botanically known as *Petunia axillaris*, and hereinafter referred to by the cultivar name Sunsnow.

The new cultivar is a product of a planned breeding program conducted by the inventor in Emerald, Victoria, Australia. The objective of the breeding program was to create new Petunia cultivars having large flowers, a spreading plant habit, and desirable flower colors.

The new cultivar originated from a cross made by the inventor of the inventor's proprietary Petunia selection No. 131077 as the male or pollen parent with the inventor's proprietary Petunia selection No. 1016 as the female or seed parent.

The cultivar Sunsnow was discovered and selected by the inventor as a flowering plant within the progeny of the stated cross in a controlled environment in Emerald, Victoria, Australia. Asexual reproduction of the new cultivar by terminal cuttings taken at Emerald, Victoria, Australia, has shown that the unique features of this new Petunia are stable and reproduced true to type in successive generations.

The cultivar Sunsnow has not been observed under all possible environmental conditions. The phenotype may vary somewhat with variations in environment such as temperature and light intensity, without, however, any variance in genotype. The following observations, measurements and comparisons describe plants grown in Emerald, Victoria, Australia, under commercial production conditions.

The following traits have been repeatedly observed and are determined to be the unique characteristics of 'Sunsnow'. These characteristics in combination distinguish 'Sunsnow' as a new and distinct cultivar:

1. White flowers that are slanted upwards.
2. Compact growth habit.
3. Decumbent and spreading plant habit.
4. Freely branching habit. Plants do not require pinching.
5. Early flowering.
6 Very floriferous with numerous flowers per plant.
7 Tolerant to rain, drought and temperature extremes.

The cultivar Sunsnow is similar in flower color to the Petunia cultivar Revolution White (disclosed in U.S. Plant Pat. No. 8,768). The cultivar Sunsnow differs from the cultivar Revolution White in the following characteristics:

1. Plants of the cultivar Sunsnow are more upright and less spreading than plants of the cultivar Revolution White.
2. Leaves of the cultivar Sunsnow are elliptic to ovate in shape whereas leaves of the cultivar Revolution White are ovate in shape.
3. Leaves of the cultivar Sunsnow are shorter than leaves of the cultivar Revolution White.
4. Sepals of the cultivar Sunsnow are narrower than sepals of the cultivar Revolution White.

5. Plants of the cultivar Sunsnow have narrower corollas than plants of the cultivar Revolution White.
6. The flower throat color of plants of the cultivar Sunsnow is white to light yellow green whereas the flower throat color of plants of the cultivar Revolution White is violet.
7. The stigma is level to the anthers on plants of the cultivar Sunsnow whereas the stigma is level or below the anthers on plants of the cultivar Revolution White.
8. The filament color of plants of the cultivar Sunsnow is green white whereas the filament color of plants of the cultivar Revolution White is white.
9. The style color of plants of the cultivar Sunsnow is yellow green whereas the filament color of plants of the cultivar Revolution White is green white.

A detailed comparison of the cultivars Sunsnow and Revolution White appears in Chart A at the end of the specification.

The accompanying colored photographs illustrate the overall appearance of the new cultivar, showing the colors as true as it is reasonably possible to obtain in colored reproductions of this type.

The first photograph comprises a side perspective view of a typical hanging basket plant of the cultivar Sunsnow.

The second photograph comprises a close-up view of individual flowers of the cultivar Sunsnow. Flower and foliage colors may appear different than the actual colors due to light reflectance.

In the following description, color references are made to The Royal Horitcultural Society Colour Chart except where general terms of ordinary dictionary significance are used. Measurements are averages from ten specimens selecfed at random from five plants.

Botanical classification: *Petunia axillaris* cultivar Sunsnow.

Parentage:

*Male or pollen parent.*—*Petunia axillaris*, inventor's proprietary selection No. 113077.

*Female or seed parent.*—*Petunia axillaris*, inventor's proprietary selection No. 1016.

Propagation:

*Type cutting.*—Terminal vegetative cuttings.

*Time to initiate roots.*—About ten days at 21C soil temperature.

*Rooting habit.*—Numerous, fine, fibrous, and well-branched.

Plant description:

*Form.*—Indeterminate, decumbent, diffuse spreading, viscid, glandular pubescent.

*Branching habit.*—Freely branching.

*Plant height.*—About 15.8 cm.

*Plant width.*—About 55 cm.

*Vigor.*—Low to moderate.

*Crop time.*—About nine weeks from a unrooted cutting to a 10.5-cm finished and flowering container.

*Foliage description.*—Leaves simple, generally symmetrical, sessile, and long persisting. Leaves at first whorled, later alternate, somewhat fleshy. Size (largest leaves): Length: About 6.7 cm. Width: About 3.7 cm. Thickness: About 1 mm. Shape: Elliptic to obovate. Aspect: Slanting upwards. Apex: Obtuse. Base: Attenuate. Margin: Entire. Texture: Sparse to moderately pubescent. Color: Young foliage upper side: 137A. Young foliage under side: 147B. Mature foliage upper side: 137A. Mature foliage under side: 147B.

*Stem description.*—Stems upright to spreading to one meter or more, hirsute. Stem diameter: About 3 mm. Internode length: Medium, about 2.3 cm. Stem color: Green, 144A.

Flower description:

*Flower type and habit.*—Large, single, salverform flowers, facing upwards, axillary. Calyx five-parted, petals united into a flower tube.

*Natural flowering season.*—Long day responsive, continuously flowers from spring through fall in Northern Hemisphere.

*Quantity.*—Numerous flowers per plant.

*Corolla.*—Diameter: About 6.2 cm. Height: About 5.5 cm. Flower tube width at distal end: About 1.7 cm. Petal quantity: Five, fused. Petal apex: Medium. Margin: Entire. Petal lobation: Medium. Undulation of margin: Medium. Texture: Pubescent on outside, smooth and satiny on inside. Color: Flower throat (inside): 155D/144C. Flower throat vein color (inside): 144A. Flower tube color (outside): 155D with hints of 144C. Flower tube vein color (outside): 144A. Petal color, inside: 155D. Petal vein color, inside: 144A. Petal color, outside: 155D. Petal vein color, outside: 144A.

*Sepals.*—Quantity: Five. Size: Length: About 2.3 cm. Width: About 6.9 mm. Shape: Spatulate. Apex: Obtuse. Margin: Entire. Texture: Pubescent. Aspect: Horizontal. Color: Inside: 137B. Outside: 137C.

*Pedicel.*—Aspect: Upright. Size: Length: About 1.7 cm. Width: About 1.8 mm. Texture: Pubescent. Color: 144A.

*Reproductive organs.*—Stigma level with anthers, superior ovary. Stamens: Stamen number: Five, four are didymous. Anther color: Cream. Filament color: Green white. Pistils: Stigma color: Green. Style color: Yellow green.

Disease resistance: No known Petunia diseases observed to date.

Fruit and seed production: Rarely observed.

*Fruit.*—Capsule with two undivided valves.

*Seeds.*—Minute, spherical.

CHART A

| CHARACTERISTIC | 'SUNSNOW' | 'REVOLUTION WHITE' |
|---|---|---|
| PLANT HEIGHT | 55 cm | 38.8 cm |
| LEAF SHAPE | Elliptic to ovate | Ovate |
| LEAF LENGTH | 6.7 cm | 7.9 cm |
| SEPAL WIDTH | 6.9 mm | 9 mm |
| COROLLA DIAMETER | 6.2 cm | 6.6 cm |
| FLOWER THROAT COLOR | 155D/144C | 82B/82C |
| STIGMA RELATIVE TO ANTHERS | Level | Level to below |
| FILAMENT COLOR | Green white | White |
| STYLE COLOR | Yellow green | Green white |

It is claimed:

1. A new and distinct cultivar of Petunia plant named 'Sunsnow', as illustrated and described.

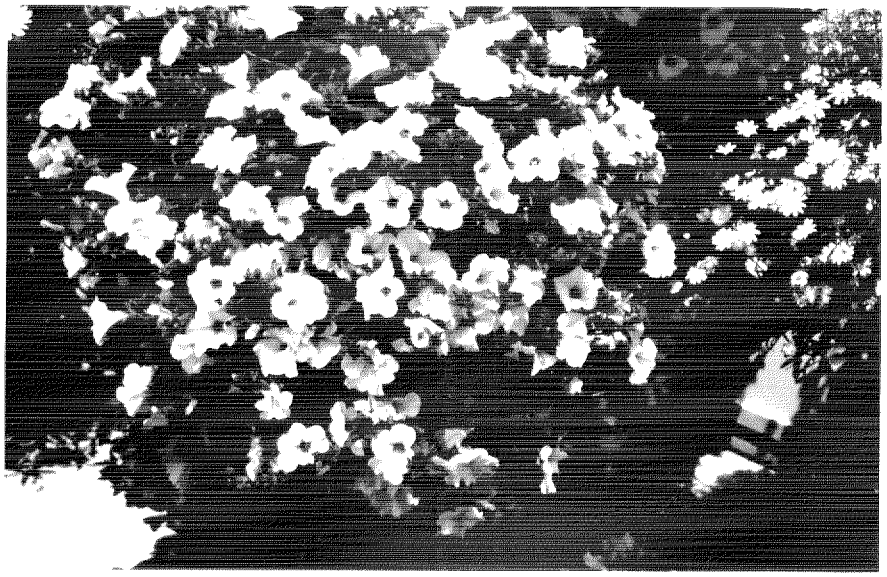

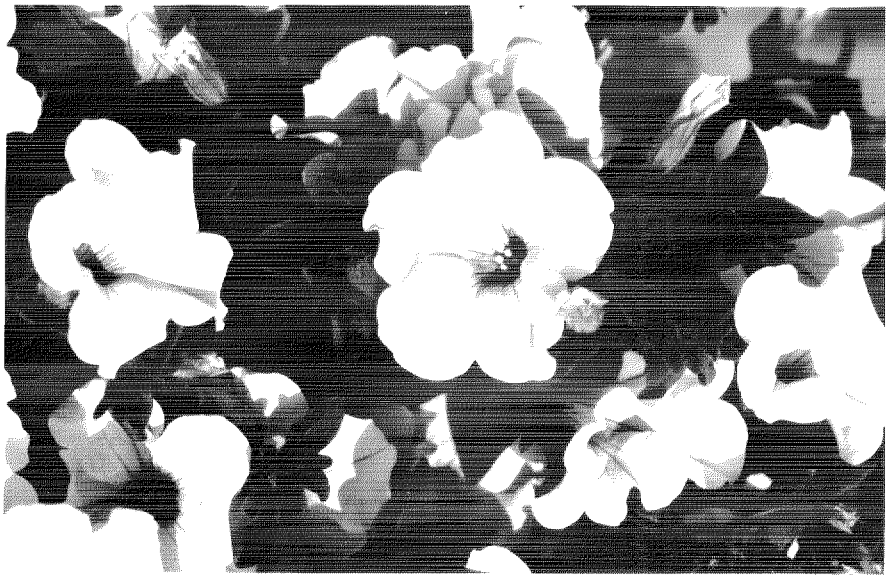

* * * * *